US006200259B1

(12) United States Patent
March (10) Patent No.: US 6,200,259 B1
(45) Date of Patent: Mar. 13, 2001

(54) METHOD OF TREATING CARDIOVASCULAR DISEASE BY ANGIOGENESIS

(76) Inventor: Keith L. March, 13800 Oakwood Ct., Carmel, IN (US) 46032

( * ) Notice: Subject to any disclaimer, the term of this patent is extended or adjusted under 35 U.S.C. 154(b) by 0 days.

(21) Appl. No.: 09/325,229

(22) Filed: Jun. 3, 1999

(51) Int. Cl.[7] .................................................. A61B 17/52
(52) U.S. Cl. ................................................................. 600/9
(58) Field of Search ........................................... 600/9–15

(56) References Cited

U.S. PATENT DOCUMENTS

| 3,890,953 | * | 6/1975 | Kraus et al. . | |
|---|---|---|---|---|
| 3,915,151 | * | 10/1975 | Kraus . | |
| 3,921,620 | * | 11/1975 | Nakayama . | |
| 4,266,532 | * | 5/1981 | Ryaby et al. . | |
| 5,401,233 | * | 3/1995 | Erickson et al. | 600/14 |
| 5,524,624 | * | 6/1996 | Tepper et al. . | |
| 5,723,001 | | 3/1998 | Pilla et al. | 607/68 |

OTHER PUBLICATIONS

Bassett, "Fundamental and Practical Aspects of Therapeutic Uses of Pulsed Electromagnetic Fields (PEMFs), " *Critical Reviews in Biomedical Engineering*, vol. 17 Issue 5 (1989), pp. 451–522.
Norton, "Pulsed Electromagnetic Field Effects on Chondroblast Culture," *Reconstr. Surg. Traumat.*, vol 19 (Karger, Basel 1985), pp. 70–86.
Detlavs et al., "Experimental study of the effects of radiofrequency electromagnetic fields on animals with soft tissue wounds," *The Science of the Total Environment*, 180 (1996), pp. 35–42.

Lin et al., "Effects of Pulsing Electromagnetic Fields on the Ligament Healing in Rabbits," *J. Vet. Med. Sci.*54(5) (1992), pp. 1017–1022.
Coats, "Pulsed electromagnetic–(short–wave) energy therapy," *Br. J. Sp. Med.*, vol. 23, No. 4 (1989), pp. 213–215.
Glassman et al., "Effect of External Pulsing Electromagnetic Fields on the Healing of Soft Tissue," *Annals of Plastic Surgery*, vol. 16, No. 4 (Apr. 1986), pp. 287–295.
Watkins, "Healing of surgically created defects in the equine superficial digital flexor tendon: Effects of pulsing electromagnetic field therapy on collagen–type transformation and tissue morphologic reorganization," *Am. J. Vet. Res.*, vol. 4, No. 10 (Oct. 1985), pp. 2097–2103.
Yen–Patton et al., "Endothelial Cell Response to Pulsed Electromagnetic Fields: Stimulation of Growth Rate and Angiogenesis In Vitro," *Journal of Cellular Physiology*, 134 (1988), pp. 37–46.

* cited by examiner

*Primary Examiner*—Max Hindenburg (57) ABSTRACT

A system and method for treating cardiovascular disease utilizes electromagnetic fields (EMF) applied by non-invasive or minimally invasive procedures. The EMF is applied to existing vascular structure to modulate blood flow and blood vessel growth in the patient. In one embodiment, a structure of electromagnetic coils is placed about a desired treatment zone to apply an EMF to the zone on the order of $10^4$–10 T. For cardiac angiogenesis, coils can be positioned on the anterior chest wall and on the back at the level of the heart. Various coil configurations are contemplated to yield appropriate field intensities at the treatment zone. In another embodiment, coils can be implanted within the patient and placed within or overlying the treatment zone. An EMF dosage plan can be developed for the patient and specific treatment zone incorporating several aspects, such as frequency components, the use of a carrier frequency, pulse shape, duty cycle, and total time exposure to the EMF.

9 Claims, 7 Drawing Sheets

METHOD OF TREATING CARDIOVASCULAR DISEASE BY ANGIOGENESIS

The present invention is directed to a method for treating cardiovascular disease by promoting growth of collateral vessels to increase blood flow to target organs and tissues.

BACKGROUND OF THE INVENTION

The major component of morbidity and mortality attributable to cardiovascular disease occurs as a consequence of the partial or complete blockage of vessels carrying blood in the coronary vascular system and in peripheral vasculature. When such vessels are occluded, various clinical syndromes may result from death of tissue previously nourished by the occluded vessels or inability of the vessels to transport sufficient blood supply to regions requiring high blood consumption and accompanying nutrients. In some individuals, blood vessel occlusion is partially compensated by the natural process of angiogenesis, in which new conduits are formed to replace the function of the impaired vessels. These new conduits, called "collateral" vessels, may facilitate restoration of blood flow to the deprived tissue, thereby constituting "natural bypasses" around the occluded vessels. However, some individuals are unable to generate sufficient collateral vessels to manage the consequences of diminished blood flow from cardiovascular disease.

At present, blood vessel occlusions are usually treated by mechanically enhancing blood flow or by medical reduction of oxygen demands in the involved tissues or organs. Mechanical enhancements are provided most commonly by (1) employing surgical techniques that attach autologous or synthetic vascular conduits proximal and distal to the areas of occlusion, thereby providing bypass grafts, or (2) revascularization by various means to physically enlarge the vascular lumen at the site of occlusion. These procedures involve such devices as balloons, endovascular knives (atherectomy), endovascular drills, and the like. The surgical approach is accompanied by significant morbidity and even mortality, while the angioplasty-type processes are complicated by recurrent stenoses in 25–35% of cases. Successful mechanical revascularization depends, inter alia, on accessibility of the occluding stenosis to such procedures. Clearly, there remains a pressing need for means to stimulate angiogenesis to provide collateral blood flow by non-invasive or minimally invasive procedures.

SUMMARY OF THE INVENTION

This invention employs electromagnetic fields (EMF) applied by non-invasive or minimally invasive procedures to modulate blood vessel growth in human or animal vasculature. In positive modulation, external application of energy fields stimulates progressive collateralization by artificially inducing or enhancing biochemical and cellular responses in the tissues permeating the target fields. In this manner, blood flow is restored to coronary and other organ systems, peripheral vasculature and muscle vascular beds through an accelerated formation and/or maturation of newly-generated and enlarged vessels that bypass partially or entirely occluded vasculature by induced angiogenesis.

From a clinical perspective, the choice to use such non-invasive revascularization would be particularly appropriate (1) in patients without reasonable options for mechanical revascularization because of inaccessible location of the stenosis, diffuse vascular disease, or poor overall medical condition for surgical or even endovascular intervention; (2) as an adjunct to surgical or endovascular interventions, in which the anatomy of the patient's blood vessels precluded revascularization of all ischemic regions (i.e., incomplete revascularization using other modalities); (3) as an adjunct to the application of other mechanical stimuli such as laser channel formation (transmyocardial laser revasularization) which have been found to reduce symptoms of ischemia; (4) as an adjunct to the administration or direct application of genetic or growth factor agents also intended to facilitate vascular growth or angiogenesis; and (5) in patients with ischemic disease and attendant symptoms who are not yet appropriate candidates for the above interventions, thereby favoring a non-invasive procedure and making possible earlier therapy attended by virtual absence of morbidity.

Potential forms of energy fields include electromagnetic fields that are pulsed over a wide range of frequencies, intensities and pulsed waveform shapes (PEMF). Electromagnetic fields may also be generated in a continuously oscillating, nonpulsed manner, thus providing a sinusoidal waveform. Specific combinations of these variables deliver a range of biological effects that can be tailored to desired results. Other energy forms, including pulsed or continuously-generated microwave-radiated energy and ultrasonic energy, may be applied. In the case of PEMF, application involves placement of coils around the regions of tissues in which collateralization is desired. One approach is to embed the coils in a cloth wrap, which may be worn as a garment surrounding the body area of interest. For cardiac applications, a vest-type garment may be fabricated. For peripheral applications a wrap, i.e., either around the leg or arm, can be designed to deliver the desired field to the affected organ or tissue.

The structure of coils contained within such garments or wraps can provide for simple homogeneous, "flat" field distributions in three-dimensional space, or may be configured to focus on fields with greater intensity localized near the target area.

The number of wire loops comprising a single coil, or each of several coils, and the electric power used to power these wire loops, should be such that the peak intensity of the field within the region of interest is on the order of $10^{-4}$–10 T.

These applications of energy fields may be utilized not only as primary therapy but in conjunction with mechanical approaches to revascularization or following standard surgical/endovascular or angioplasty approaches. For example, where such revascularization is partially but inadequately achieved by standard techniques, externally-based fields provide an opportunity for complementary revascularization of target areas.

Apparatus for delivering the desired electromagnetic stimulation to target areas taught herein are readily adapted from well-reported (FMF) technology relating to the skeletal system. Principles of design are to be found, for example, in U.S. Pat. Nos. 5,401,233, 4,266,532, 3,890,953 and 3,915,151. This applies not only to the basic structure employed in the delivery system but also for the ranges of parameters, as discussed herein. Of particular interest for its comprehensive coverage of electromagnetic therapy is Bassett, "Fundamental and Practical Aspects of Therapeutic Uses of Pulsed Electromagnetic Fields (PEMFs)," *Critical Reviews in Biomedical Engineering,* 17:451, Issue 5 (1989). Also of interest in refining parameters based on target location and environment, are the following: Norton, "Pulsed Electromagnetic Field Effects on Chondroblast Culture," *Reconstr. Surg. Tramaut.,* 19:70 (1985); Detlays et al., "Experimental Study of the Effects of Radiofrequency Electromagnetic Fields on Animals With Soft Tissue Wounds," *Sci. of Total Environ.*, 180:35 (1996); Lin et al., "Effects of Pulsing Electromagnetic Fields on the Ligament Healing in Rabbits, "*J. Vet. Med. Sci.* 54(5):1017 (1992); Goats, "Pulsed Electromagnetic-(short-wave) Energy Therapy," *Br. J. Sp. Med.* 23:213; Glassman et al., "Effect of External Pulsing Electromagnetic Fields on the Healing of Soft Tissue," *Annals of Plast. Surg.* 16(4):287 (April 1986); Watkins et al., "Healing of Surgically Created Defects in the Equine Superficial Digital Flexor Tendon: Effects of Pulsing Electromagnetic Field Therapy on Collagen-type Transformation and Tissue Morphologic Reorganization," *Am. J. Vet. Res.* 46(10):2097 (1985), and Zoltan, "Electrical Stimulation of Bone: An Overview," *Seminars in Orthopaedics* 1(4):242 (1986).

The use of PEMF and local application of ultrasonic energy have been described as providing enhancement of fusion rates of bony fractures, as well as accelerating rates of wound healing. U.S. Pat. No. 5,524,624. Such procedures have shown significant promise in diabetes, tobacco use, or other conditions which appear to deter natural bone healing or wound healing responses. They have, however, suggested no extension of the electromagnetic phenomenon in circumstances where positive or negative modulation of angiogenesis can provide dramatic opportunities for addressing problems of (1) occlusions in the coronary and other organ systems and peripheral vasculature, and (2) blood-dependent tumorous tissues.

GENERAL DESCRIPTION

It is important, in the application of electromagnetic fields to facilitate or prevent angiogenesis, that the body's region of interest be subjected to an essentially homogeneous electrical field for maximum efficacy and safety. This means that the treatment field should have specific spatial and temporal characteristics. To achieve this focused treatment environment with deep tissue penetration, pulsed EMF is preferred.

Spatial Characteristics

An apparatus is designed to deliver PEMF with the appropriate spatial characteristics for treatment of the region of focus in three dimensions. For example, the field must be sufficiently homogeneous with respect to biological effects throughout the cardiac volume in the case of coronary angiogenesis or other target areas.

A degree of spatial specificity is assured by the fact that ischemic tissues possess increased sensitivity to a variety of proangiogenic stimuli. Accordingly, regions of the muscle or surrounding organs which are not actively ischemic by virtue of limited blood flow would not be expected to respond to PEMF as readily as ischemic tissues. In ischemic tissues, a variety of other receptor and growth factor gene expressions occur in response to the ischemia, thereby conferring enhanced sensitivity on the field. High resolution of the spatial characteristics of the field to restrict exposure to target tissues are usually not necessary. Instead, it is sufficient that adequate field amplitude be directed to the target region to provide a stimulus that is greater than a threshold required to yield a desired biologic response.

One approach for providing the desired PEMF signal to the target tissue volume, either including the heart, or peripheral musculature, is the use of paired (Helmholtz) coils which are placed in a parallel configuration separated by a distance approximately similar to the diameter of the coils, so that the space between the coils encompasses the target volume for treatment. The coils are then energized simultaneously. This arrangement results in a substantially homogeneous field within the target volume, which will thus produce biologically significant effects therein. For cardiac angiogenesis, coils would be positioned on the anterior chest wall and on the back, at the level of the heart.

Figure 1A:
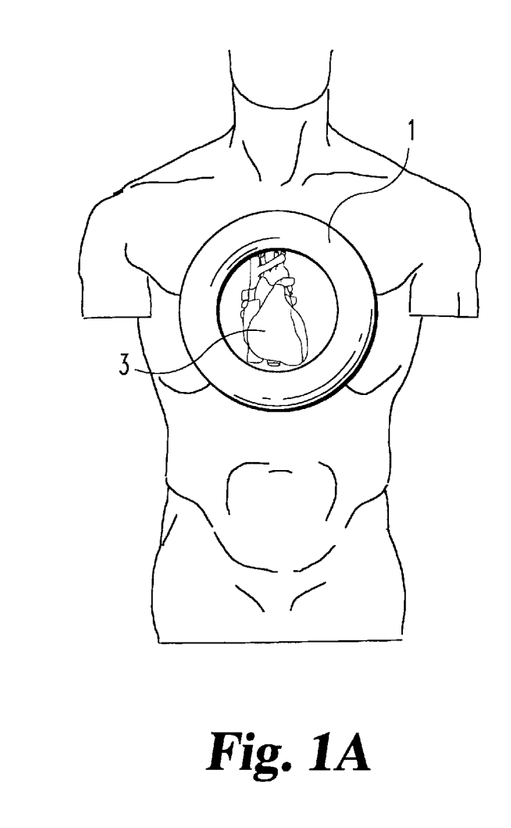
FIGS. 1A–1C are diagrammatic representations of anterior, side and posterior views of a human heart and torso with anterior and posterior coils in accordance with one embodiment of the present invention.
Figure 1B:
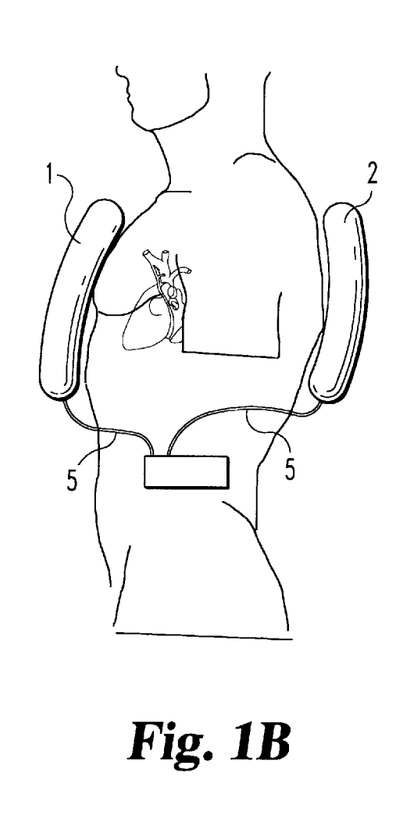
Figure 1C:
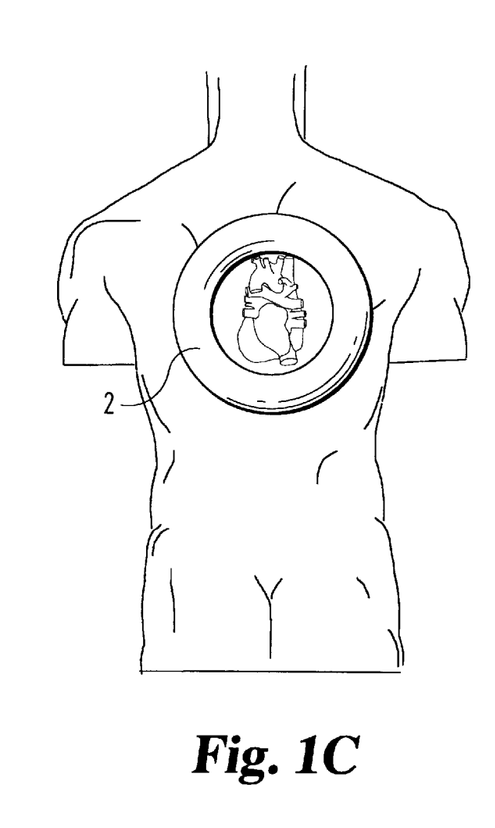

FIG. 1 depicts a human torso containing a heart. FIG. 1A shows anterior 1 and posterior 2 coils as described, with diameters slightly larger than cardiac silhouette 3, and similar to the anterior-posterior distance between the two coils. FIG. 1B, with the arm raised, demonstrates that the anterior 1 and the posterior 2 coils are placed so as to encompass the cardiac region in the volume subtended by the two coils. FIG. 1C shows posterior coil 2, again with diameter similar to that of anterior coil 1 and to the distance separating the two coils. FIG. 1B also shows a pulse generator box 4, consisting of a power supply, an appropriate circuitry designed to generate pulses to energize the coils, and an amplifier apparatus as necessary to amplify these pulses to the desired energies. Also shown in FIG. 1B are leads 5 running from the pulse generator/amplifier circuitry box 4 to the paired coils 1 and 2. The generator box 4 and leads 5 are present but not shown in FIGS. 2–7.

Where less field homogeneity is required for the treatment of the target volume, a single coil on the anterior or posterior surface of the thorax may be used. Such a coil provides a field of an intensity that decreases as the distance from the surface of the coil increases. This simpler approach is feasible because it has been determined that the biological effects of PEMF are relatively amplitude-insensitive. In that case, the decrement and intensity distance from the coil may be comparatively unimportant to achieve the desired effect.

Figure 2A:
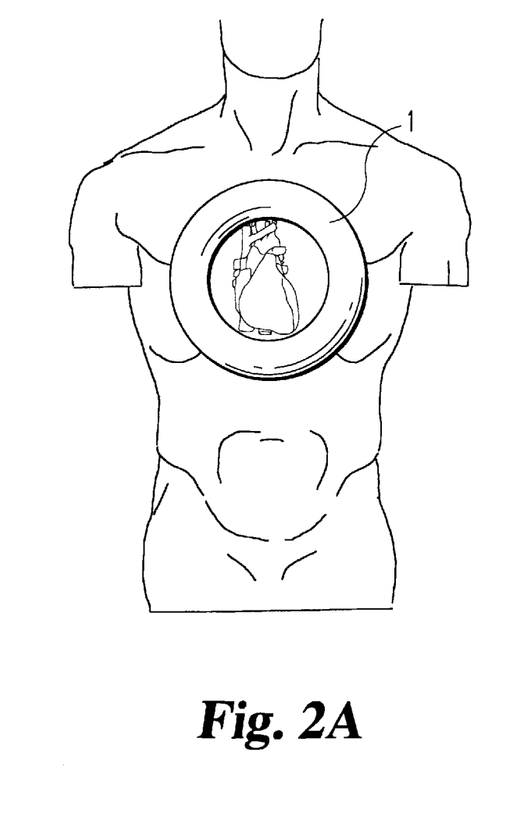
FIGS. 2A–2C are diagrammatic representations of anterior, side and posterior views of a human heart and torso with an anterior coil only in accordance with a further embodiment of the present invention.
Figure 2B:
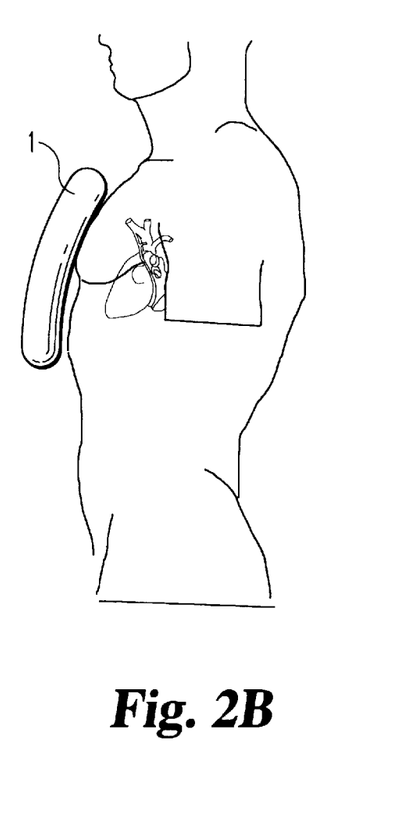
Figure 2C:
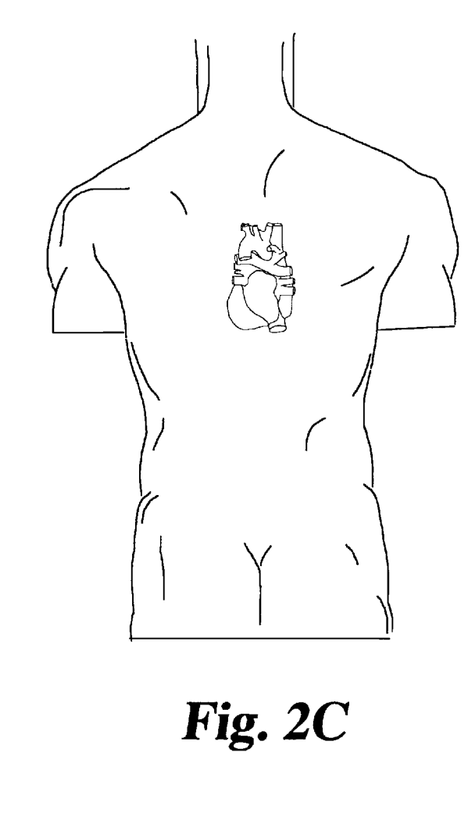

FIG. 2 depicts a single coil 1, placed on the anterior aspect of the chest, again with diameter so it would be greater than that of the cardiac silhouette.

To enhance focus of PEMF intensity in the cardiac region, an asymmetric configuration comprising a bent oval wrapped from the anterior thorax along the left side of the body may be used to encompass within its field a geometric space that includes the heart.

Figure 3A:
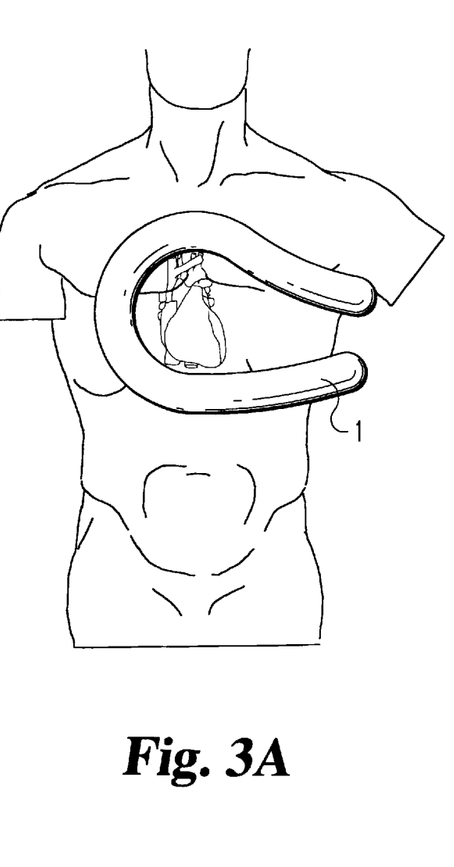
FIGS. 3A–3C are diagrammatic representations of anterior, side and posterior views of a human heart and torso with coil having a bent oval configuration in accordance with another embodiment of the present invention.
Figure 3B:
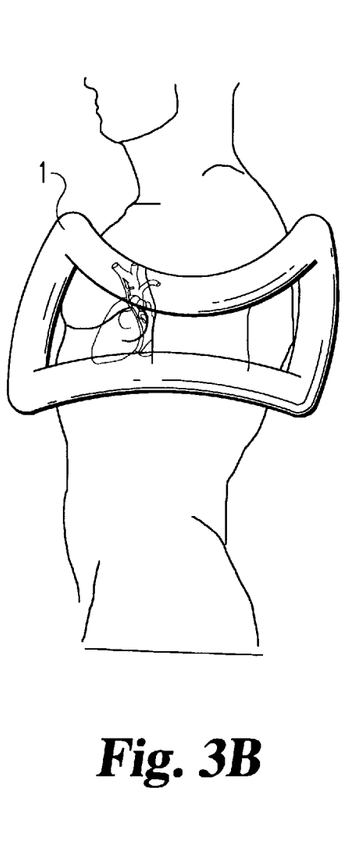
Figure 3C:
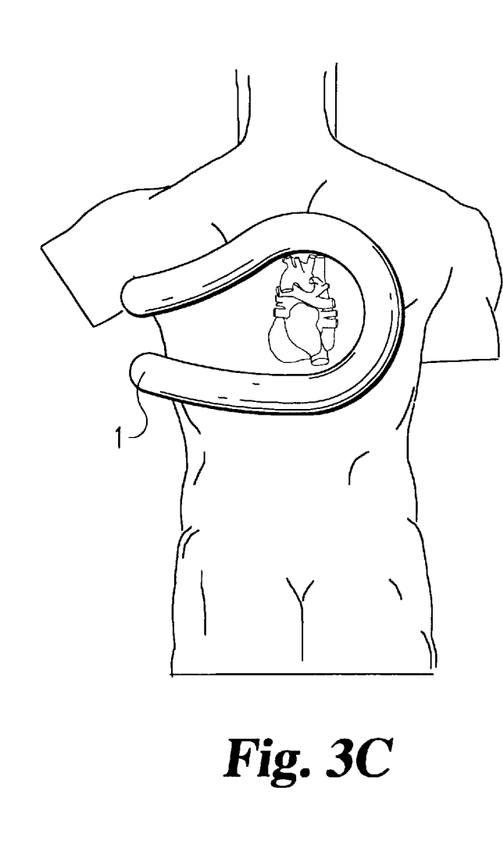

FIG. 3 depicts a bent oval configuration for the single coil 1, which provides a wrap extending from the anterior view in FIG. 3A, around the left aspect of the thorax as seen in FIG. 3B, and onto the back as in FIG. 3C, thus encompassing the heart volume within its bent shape.

Another means for enhancing field focus is to provide intensity and specificity in the cardiac region by a comparatively small anterior coil and a comparatively large posterior coil, causing the more anteriorly-located heart to receive the greater intensity of field strength.

Figure 4A:
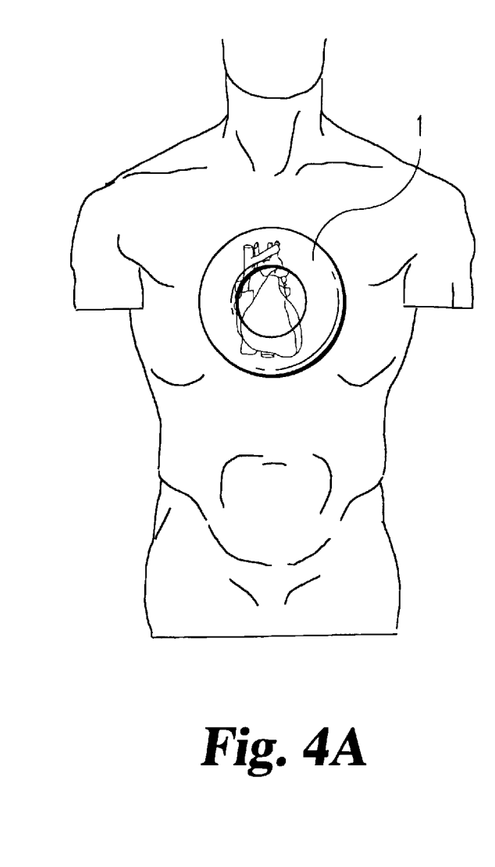
FIGS. 4A–4C are diagrammatic representations of anterior, side and posterior views of a human heart and torso with an anterior coil and a larger posterior coil in accordance with yet another embodiment of the present invention.
Figure 4B:
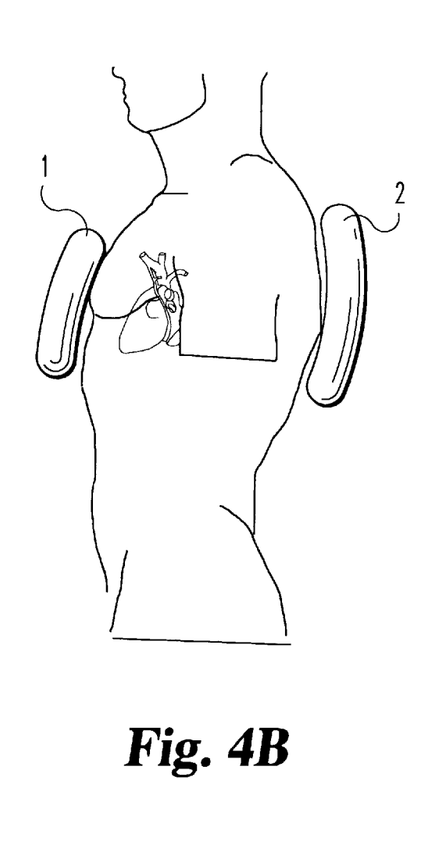
Figure 4C:
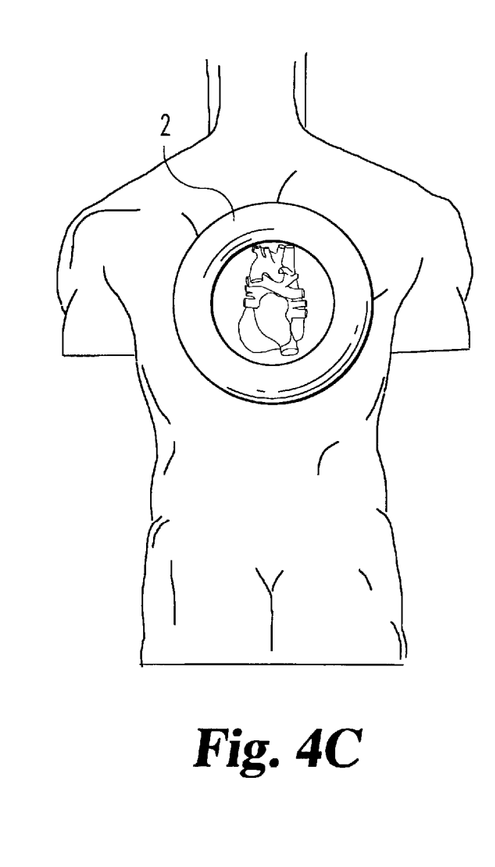

FIG. 4 demonstrates a comparatively small anterior coil 1 positioned over the heart, thus providing for an increase in the volume-specific field intensity in the anterior aspect of the thorax, closer to the location of the cardiac volume. FIG. 4C also shows this smaller coil 1 placed anteriorly and a larger coil 2 placed posteriorly. FIG. 4B further shows larger coil 1, which produces a diminished field intensity as the back is approached.

Enhanced PEMF effects in the cardiac region in comparison to other areas of the thorax may also be provided by intermittent application of a PEMF using anterior and posterior coils alternating with PEMF employing left and right-sided coil placements. Here, the fields with alternate interaction from the anterior-posterior and the side-to-side direction provide a convergence of both fields upon the cardiac volume. Tissues on the left or right or anterior and posterior to the heart would receive less intense fields because they would not be at the intersection of the "field cylinders."

Figure 5A:
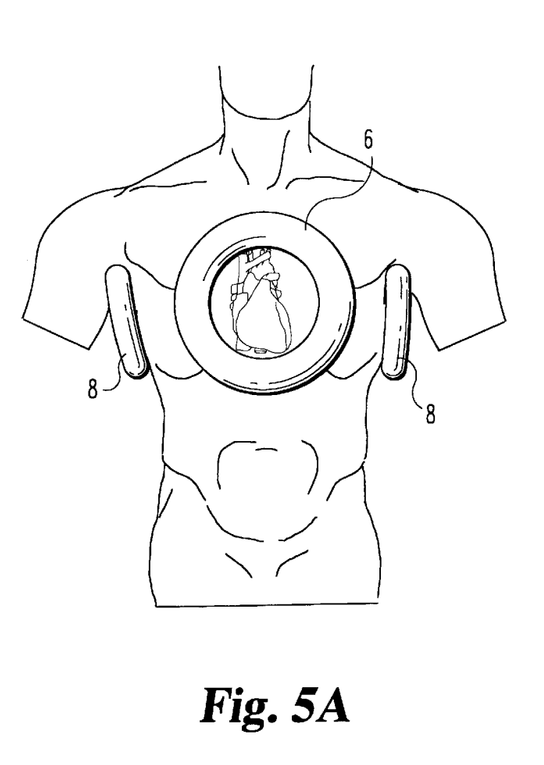
FIGS. 5A–5C are diagrammatic representations of anterior, side and posterior views of a human heart and torso with two sets of coils in accordance with an alternative embodiment of the present invention.
Figure 5B:
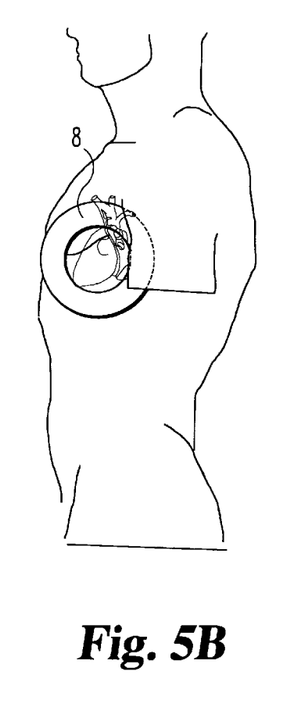
Figure 5C:
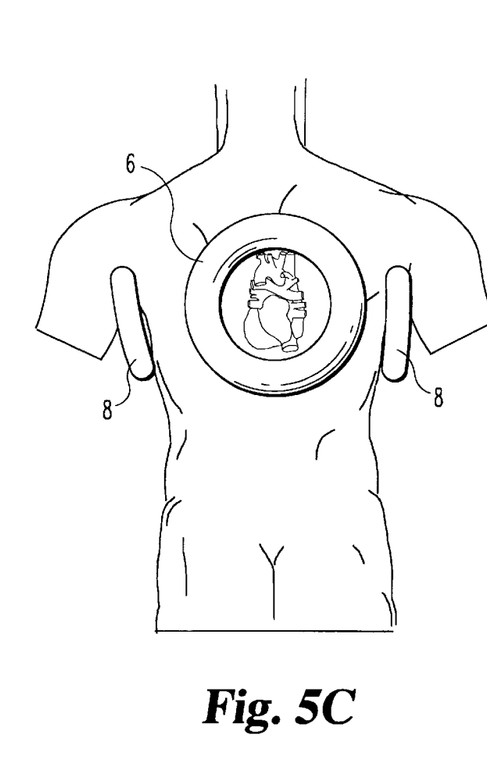

FIG. 5 shows two pairs of coils, with an anterior 6 and posterior 7 pair of coils, respectively, in the anterior and posterior views in FIGS. 5A and 5C, and a left/right pair of coils 8 seen both from the front and back in FIGS. 5A and 5C. The left coil is best seen in FIG. 5B. These would be energized so that the anterior/posterior pair would initially create a field, alternating with a field created between the left and right pair of coils. Accordingly, the tissue volume that would receive the maximal energy exposure would be the cardiac volume occurring at the intersection of the cylinders described by the two coil pairs in FIGS. 5A and 5C. FIG. 6 shows a pair of coils implanted either within or overlying the pericardial sac for maximal spacial proximity to the cardiac tissue.

Enhanced spatial localization of the PEMF to the region of the heart may also be achieved while limiting exposure of other tissues by use of a single coil, or one or both of a pair of coils placed in the body by surgical or minimally-invasive methods. One or more such cells are placed in geometric proximity to the cardiac structure. Such coils would preferably be in opposition to the heart surface, either outside or inside the pericardial space. In this way, the heart structures would receive the maximum geometrically feasible localization as compared to the adjacent thoracic structures.

Figure 6A:
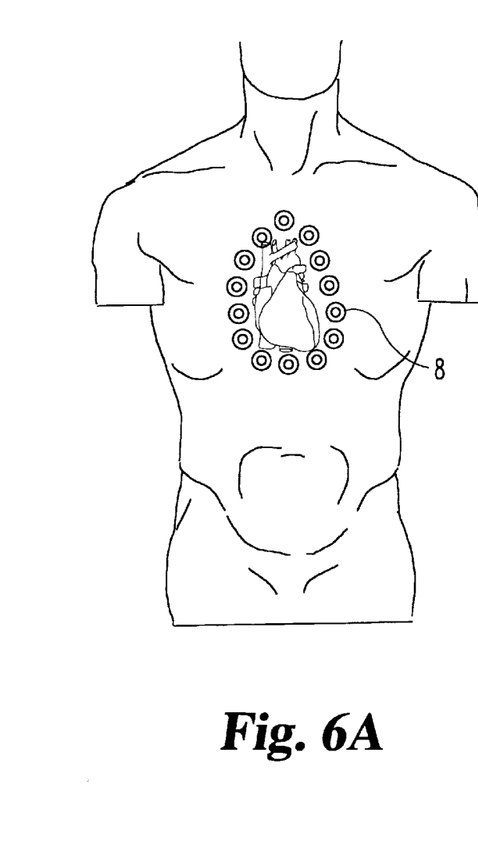
FIGS. 6A–6C are diagrammatic representations of anterior, side and posterior views of a human heart and torso with coils vertically positioned adjacent the pericardial sac in accordance with an additional embodiment of the present invention.
Figure 6B:
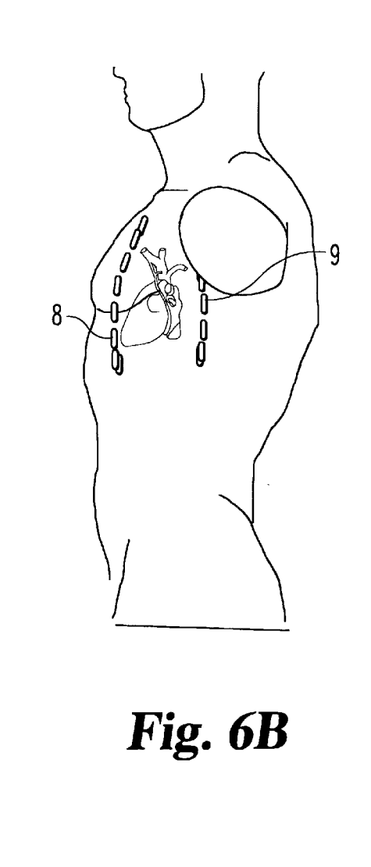
Figure 6C:
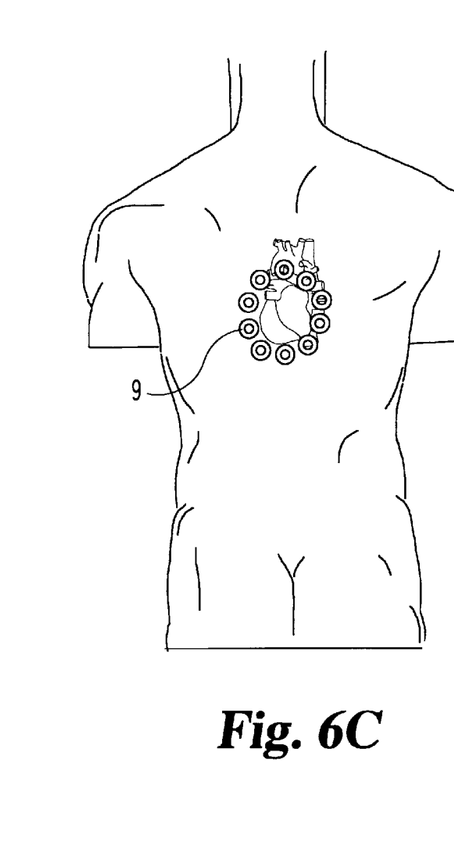

FIG. 6 shows coils 8 and 9 placed in a vertical plane, seen both from the anterior and back views in FIGS. 6A and 6C, as well as in FIG. 6B.

Further shaping of the PEMF field in three dimensions is possible by utilizing structures of variable permeability to the electromagnetic fields placed as specific shields on the thoracic body wall, in conjunction with coils similarly placed. These shields, consisting of thin (1–100 micron) layers of material incorporating ferromagnetic or other similar materials, would be placed between the coil surfaces and the body wall. Selective placement of such shields makes it possible to focus the field intensity on the desired tissue volume while diminishing its intensity in other regions.

Figure 7A:
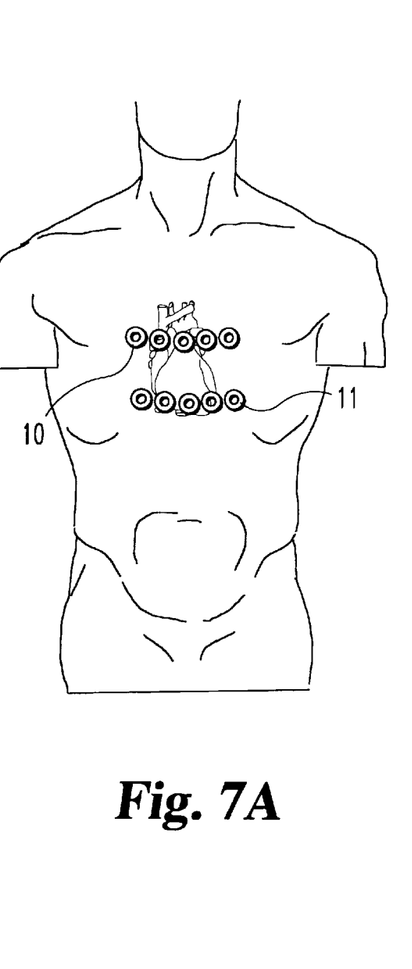
FIGS. 7A–7C are diagrammatic representations of anterior, side and posterior views of a human heart and torso with coils horizontally positioned adjacent the pericardial sac in accordance with an additional embodiment of the present invention.
Figure 7B:
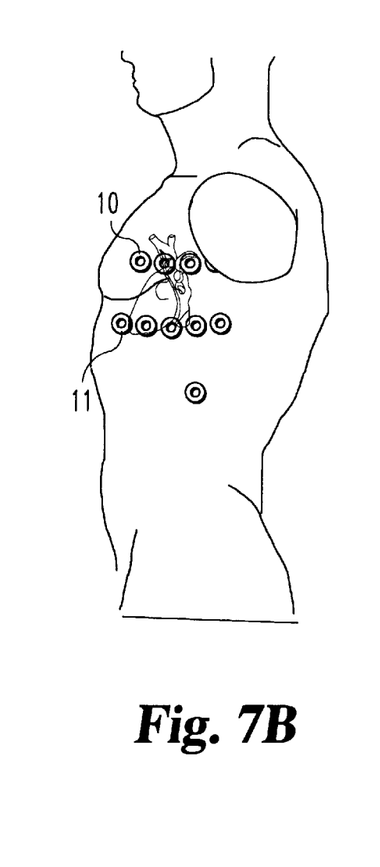
Figure 7C:
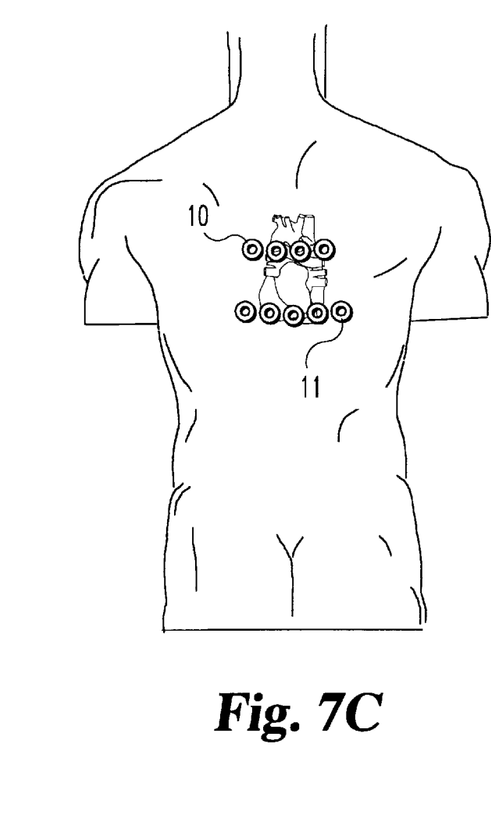

FIG. 7 depicts an alternative positioning for implanted coils to be placed within or overlying the pericardial sac, in the horizontal plane. In FIG. 7, two coils 10 and 11 are seen encircling the heart at its base (the lower portion), as well as at its apex (the upper portion). These coils may be seen from the front, (FIG. 7A), left (FIG. 7B) and back (FIG. 7C) to encircle the cardiac volume.

Temporal Characteristics

The temporal characteristics of a PEMF dosage plan includes several aspects: (1) individual frequency components of the employed fields, (2) the presence or absence of a "carrier" frequency which may be modulated with a frequency of lower value; for example, a carrier frequency of 100 KHz–10 GHz might be modulated or pulsed with a frequency of 20–10,000 Hz, (3) the particular shape of the pulses, expressed as electromagnetic energy varying with time, (4) the "duty cycle" of the pulsing field, i.e., whether the variable fields are applied continuously or in "burst" patterns with intermittent periods of no electrical fields, (5) the total time of bodily exposure to the field-generating device on a daily basis, and (6) the number of days over which the device is to be utilized in a treatment plan. Several of these variables have preferred ranges which have been defined by observation of biological responses both in vitro and in vivo.

Alternatively, dual or multiple sinusoidal frequencies in a serial or parallel combination may be provided as non-sinusoidal pulse wave forms which may be square, triangular, or intermediate in shape. Such non-sinusoidal wave forms contain within them a variety of frequencies which comprise the overall shape, as defined by a Fourier transform, revealing contained frequency components of simple sinusoidal frequencies. Accordingly, a single repetition rate of a non-sinusoidal wave-form can contain numerous inherent sinusoidal frequency components, and a range of frequencies within this domain of frequencies thus provides an efficacious biological response. Such pulsed waveforms are typically employed at repetition rates within the range of 20–4,000 hertz but may incorporate frequency components up to 10 GHz. To conserve energy from portable batteries or power pack systems, limited duty cycles of the pulsed field are employed for periods of time from 10–100% of total time. Time or exposure to the device ranges from 1–24 hours per day, preferably from about 1–6 hours per day.

PREFERRED EMBODIMENT

A device for treatment of the coronary vasculature comprises a thinly configured set of coils and power supply sufficiently compact to be worn underneath either while the patient is ambulatory and active or at rest. Each of a pair of coils is positioned anterior and posterior to the region requiring angiogenic facilitation of cardiac vessels or tissues. Optimal positioning of the coils is slightly left of midline on the anterior chest wall and on the back, at the level of the heart. Diameters of these coils range approximately from 10–15 centimeters. However, they may be smaller, or, in fact, encompass virtually the entire chest. Homogeneity of the electric field intensity is obtained for pairs of coils when spaced at a coil separation approximating the diameter of the coils. Accordingly, one optimal coil diameter is configured to the anterior-posterior thickness of the subject's chest. A reasonably homogeneous field would thereby be provided to the entire cardiac tissue volume.

The coils are comprised of wire wrappings providing peak magnetic fields of 10 $\mu$T–5 T, as measured in the treatment region between the coils when energized. These wire wrappings are placed within a thin, flexible containing material such as of plastic, cloth, or rubber which may be worn on the body underneath clothing, with a minimum of discomfort. The coils are connected by power supply wires to a pulse generator which is also worn beneath the clothes, and may be placed in apposition to one of the coils. The pulse generator is energized during the time periods of treatment, typically 1–16 hrs/day, especially 1–4 hrs/day, and provides energy to the coils with a temporal configuration which results in positive vascular growth modulation. Such signals may be pulsed with repetition rates of 20–4000 Hz, with emissions of bursts of pulses occurring 1–50 times each second. The pulse bursts may include from 10–100 discrete pulses, or alternatively the pulses may be provided throughout the time period, without a burst timing. The pulse generator may be programmed for the desired treatment modality to be automatically provided for the selected time period, once activated by the patient, with a mechanism to ensure power-down at the correct time.

In like manner, the methods of this invention may be adapted by those skilled in the arts involved to treat blockages of vessels in the peripheral vasculature by noninvasive or minimally-invasive procedures.

What is claimed is:

1. A method for modulating blood vessel growth in targeted coronary vasculature comprising:
    applying an electromagnetic field (EMF) to the desired treatment zone to modify blood flow thereto.
2. A method for modulating blood vessel growth in targeted coronary vasculature comprising:
    applying an electromagnetic field (EMF) to the desired treatment zone to modify blood flow thereto in which the EMF is induced by pulsed DC or AC current.
3. The method of claim 2 in which EMF is applied in conjunction with mechanical revascularization.
4. The method of claim 3 in which EMF is applied in conjunction with angioplasty.
5. The method of claim 2 in which FMF is applied in conjunction with administration or direct application of genetic or growth factor agents to facilitate vascular growth or angiogenesis.
6. The method of claim 2 in which EMF is applied in conjunction with transmyocardial mechanical or laser revascularization.
7. A method for modulating blood vessel growth in targeted peripheral vasculature comprising:
    applying an electromagnetic field (EMF) to the desired treatment zone to modify blood flow thereto in which the EMF is induced by pulsed DC or AC current, and in which EMF is applied in conjunction with mechanical revascularization.
8. The method of claim 7 in which EMF is applied in conjunction with angioplasty.
9. A method for modulating blood vessel growth in targeted peripheral vasculature comprising:
    applying an electromagnetic field (EMF) to the desired treatment zone to modify blood flow thereto in which the EMF is induced by pulsed DC or AC current, and in which EMF is applied in conjunction with administration or direct application of genetic or growth factor agents to facilitate vascular growth or angiogenesis.

* * * * *

UNITED STATES PATENT AND TRADEMARK OFFICE
CERTIFICATE OF CORRECTION

PATENT NO.    : 6,200,259 B1
DATED         : March 13, 2001
INVENTOR(S)   : Keith L. March Page 1 of 1

It is certified that error appears in the above-identified patent and that said Letters Patent is hereby corrected as shown below:

<u>Column 2,</u>
Line 53, replace "(FMF)" with -- (EMF) --

<u>Column 6,</u>
Line 53, replace "underneath" with -- underneath clothing, --

Signed and Sealed this

Sixteenth Day of October, 2001

Attest:

*Nicholas P. Godici*

NICHOLAS P. GODICI
*Attesting Officer*   *Acting Director of the United States Patent and Trademark Office*